United States Patent [19]

Gschwend

[11] 4,022,800
[45] May 10, 1977

[54] 2-PYRAZOLYL-BENZOPHENONES

[75] Inventor: Heinz Werner Gschwend, New Providence, N.J.

[73] Assignee: Ciba-Geigy Corporation, Ardsley, N.Y.

[22] Filed: Aug. 28, 1975

[21] Appl. No.: 608,796

Related U.S. Application Data

[63] Continuation-in-part of Ser. No. 475,475, June 3, 1974, Pat. No. 3,939,271.

[52] U.S. Cl. .............................. 260/310 R; 260/311; 260/247.5 E; 260/243 B; 260/247.1 M; 260/268 H; 260/293.7; 260/295.5 S; 424/273
[51] Int. Cl.² ............ C07D 231/12; C07D 295/00; C07D 401/00
[58] Field of Search ........ 260/310 R, 311, 247.5 E, 260/247.1 M, 268 H, 293.7, 295.5 S, 243 B; 424/273

[56] References Cited

UNITED STATES PATENTS 3,939,271  2/1976  Gschwend .......................... 424/273

FOREIGN PATENTS OR APPLICATIONS 2,524,048  1/1976  Germany

*Primary Examiner*—Donald B. Moyer
*Attorney, Agent, or Firm*—Joseph G. Kolodny; Theodore O. Groeger; John J. Maitner

[57] ABSTRACT

2-Pyrazolyl-benzophenones, e.g. those of the formula

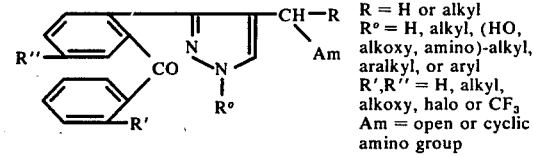

R = H or alkyl
R° = H, alkyl, (HO, alkoxy, amino)-alkyl, aralkyl, or aryl
R',R'' = H, alkyl, alkoxy, halo or CF₃
Am = open or cyclic amino group corresponding ketals, carbinols, acyl derivatives or therapeutically useful acid addition salts thereof exhibit antianxiety and anti-depressant effects.

5 Claims, No Drawings

2-PYRAZOLYL-BENZOPHENONES

CROSS-REFERENCE TO RELATED APPLICATION

This is a continuation-in-part of application Ser. No. 475,475, filed June 3, 1974, now U.S. Pat. No. 3,939,271.

SUMMARY OF THE INVENTION

The present invention concerns and has for its object the provision of new 2-(3- or 5-pyrazolyl)-benzophenones or -thiophenones, their ketals or carbinols correpsonding to Formulae I and II

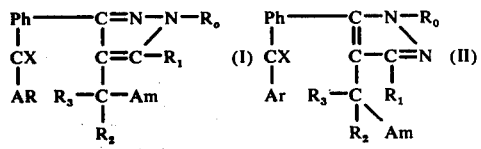

wherein Ph is a 1,2-phenylene radical, Ar is a monocyclic, carbocyclic aryl radical, $R_o$ is hydrogen, lower alkyl, (hydroxy, lower alkoxy or Am)-$C_mH_{2m}$ or Ar-$C_nH_{2n}$, Am is an open or cyclic amino group, m is an integer from 1 to 7, n such from 0 to 7, each of $R_1$, $R_2$ and $R_3$ is hydrogen or lower alkyl, and X is oxo, thio, or hydrogen and hydroxy or lower alkoxy; a simple or mixed, open or cyclic lower alkyl or alkylene ketal thereof; or a lower alkanoyl, alkoxycarbonyl, AmCO or AmCS derivative of the compounds containing at least one hydrogen attached to oxygen or nitrogen; or a therapeutically useful acid addition salt thereof; as well as corresponding pharmaceutical compositions and of methods for the preparation and application of these products, which are useful antianxiety and antidepressant agents.

DESCRIPTION OF THE PREFERRED EMBODIMENTS

The 1,2-phenylene radical Ph, as well as the aryl radical Ar, are unsubstituted or substituted by one or more than one, preferably by one or two, of the same or different substituents selected from the group consisting of lower alkyl, e.g. methyl, ethyl, n- or i-propyl or -butyl; etherified or esterified hydroxy, such as lower alkoxy, e.g. methoxy, ethyoxy, n- or i-propoxy or -butoxy; or halo, e.g. fluoro, chloro or bromo; or trifluoromethyl. The term "lower", referred to above and hereinafter in connection with organic radicals or compounds respectively, defines such with up to 7, preferably up to 4, carbon atoms.

Preferred 1,2-phenylene radicals Ph are 1,2-phenylene, (lower alkyl)-1,2-phenylene, (lower alkoxy)-1,2-phenylene, (halo)-1,2-phenylene or (trifluoromethyl)-1,2-phenylene and preferred aryl radicals Ar are phenyl, (lower alkyl)-phenyl, (lower alkoxy)-phenyl, mono- or di-(halo)-phenyl or (trifluoromethyl)-phenyl.

The radical $R_o$ preferably represents hydrogen, lower alkyl or Ar-$C_nH_{2n}$, wherein n is an integer from 0 to 7, preferably 1 to 4. It may also represent (hydroxy, lower alkoxy or Am)-$C_mH_{2m}$ wherein m is an integer from 1 to 7 and Am is exemplified by amino, mono- or di-lower alkylamino, lower alkyleneimino or mono-aza-, oxa- or thiaalkyleneimino, wherein the additional nitrogen, oxygen or sulfur atom is separated from the imino-nitrogen by at least 2 carbon atoms, e.g. mono- or di-(methyl, ethyl, n- or i-propyl or -butyl)-amino; pyrrolidino, piperidino or hexamethyleneimino; piperazino, 4-(lower alkyl, e.g. methyl or ethyl)-piperazino; morpholino or thiamorpholino. Preferred amino groups Am are mono-or di-lower alkylamino, pyrrolidino, piperidino, piperazino, 4-(lower alkyl)-piperazino or morpholino.

The radicals $R_1$, $R_2$ and $R_3$ represent preferably a hydrogen atom, but also lower alkyl, above all methyl.

The ketals of said benzophenones or -thiophenones are either simple ketals or thioketals, or mixed ketals, containing oxygen and sulfur, and are derived either from lower alkanols or -thiols, or lower alkylene glycols or thioglycols respectively. Thus, X represents, for example, two members selected from methoxy, ethoxy, n- or i-propoxy, methyl- or ethylmercapto; or one member of 1,2-ethylenedioxy, 1,2- or 1,3-propylenedioxy or -thioxy.

Said acyl derivatives are either esters of said carbinols and/or amides of said primary or secondary Am-compounds, and the lower alkanoyl derivatives are exemplified by formyl, acetyl, propionyl or pivalyl derivatives; lower alkoxycarbonyl derivatives by methoxy-, ethoxy-, n- or i-propoxy- or -butoxycarbonyl derivatives; and AmCO and AmCS derivatives are preferably those of NH-compounds.

The compounds of the invention exhibit valuable pharmacological properties, for example, antianxiety and especially anti-depressant effects, differing from those of imipramine. This can be demonstrated in animal tests, using advantageously mammals, such as mice, rats or monkeys, as test objects. The compounds of the invention can be applied to the animals enterally, e.g. orally, or parenterally, such as subcutaneously or intraperitoneally, e.g. in the form of aqueous solutions or starchy suspensions. The dosage may range between about 0.1 and 300 mg/kg/day, preferably between about 1 and 100 mg/kg/day, advantageously between about 2 and 20 mg/kg/day. An antidepressant effect is observed, for example, in the amphetamine interaction test (P. Carlton, Psychopharmacologia 1961, Vol II, p. 364) performed with male albino rats, which are trained to press a bar every 30 seconds, in order to avoid an electric shock applied through the floor grid. In case the animals receive i.p. 0.25 mg/kg/day of amphetamine, their performing rate for avoiding said shocks during a test period or about 4–5 hours is slightly higher than that of placebo (saline) treated animals. In case the animals receive the compounds of the invention (or imipramine for control purposes) in the above-mentioned doses, preferably at 5 or 10 mg/kg/day i.p. and about 45 minutes later the amphetamine, their rate of avoiding the shocks is highest, as compared with that of rats receiving a) saline alone, b) saline and amphetamine, or c) the compounds of the invention and saline. In addition the compounds of the invention exhibit antianxiety effects in rats or squirrel monkeys, advantageously at dosages between about 2 and 20 mg/kg/day. Accordingly, they reduce acquired fear or anxiety associated with a psychological conflict. It is established by simultaneously rewarding with food and punishing with electric shock all lever-pressing responses of the animals made in the presence of a discriminative tone stimulus. For example, rats first learn to press a lever to obtain a milk reward, which is delivered on the average of once per two minutes. After this schedule, which lasts fifteen minutes, a tone stimulus of three minute duration is presented. The stimulus signals a change from a variable interval schedule of reinforcement, to a continuous reinforcement schedule (CRF). During the CRF schedule, all lever responses not only produce milk rewards but also an electric shock to the animals' feet. During the period in which a shock accompanies the food reward, the tone stimulus produces a suppression of all lever pressing responses. Thus, for example, administration of 5-chloro-2-(1-methyl-4-aminomethyl-5-pyrazolyl)-2'-fluorobenzophenone mono phosphate, a characteristic compound of the invention applied at about 5 mg/kg/day intraperitoneally to rats or orally to squirrel monkeys, reinstate these responses, indicating that the animals tolerate more shocks in obtaining the food reinforcement. Accordingly, the compounds of the invention are especially useful in combatting depression and anxiety. Moreover, they are also valuable intermediates in the preparation of other useful products, especially of pharmacologically active compounds.

Particularly useful are compounds of Formulae I and II, in which Ph is 1,2-phenylene, (lower alkyl)-1,2-phenylene, (lower alkoxy)-1,2-phenylene, (halo)-1,2-phenylene or (trifluoromethyl)-1,2-phenylene, Ar is H-Ph, $R_o$ is hydrogen, lower alkyl, (hydroxy, lower alkoxy or Am)-$C_mH_{2m}$, or Ar-$C_nH_{2n}$, Am is amino, mono- or di lower alkylamino, or five to seven ring-membered lower alkyleneimino, m is an integer from 2 to 4, and n such from 0 to 4, each of $R_1$, $R_2$ and $R_3$ is hydrogen or lower alkyl and X is oxo, thio, or hydrogen and hydroxy or lower alkoxy, or the simple or mixed, open or cyclic lower alkyl or alkylene ketals thereof, or lower alkanoyl, alkoxy-carbonyl, AmCO or AmCS derivatives of the compounds containing at least one hydrogen attached or oxygen or nitrogen, or a therapeutically useful acid addition salt thereof.

Preferred compounds of the invention are those of Formula I and II, wherein Ph is 1,2-phenylene, (alkyl)-1,2-phenylene or (halo)-1,2-phenylene, Ar is H-Ph, $R_o$ is hydrogen, alkyl, 2- or 3-(hydroxy or dialkylamino)-(ethyl or propyl) or H-Ph-methyl, each of $R_1$, $R_2$ and $R_3$ is hydrogen or methyl, the group Am is amino or dialkylamino, X is oxo, thio, two alkoxy groups, one alkoxy and alkylmercapto group, or ethylenedioxy, or an alkanoyl derivative of the compounds containing at least one hydrogen attached to oxygen or nitrogen, in which compounds alkyl, alkanoyl, alkoxy or alkylmercapto has up to 4 carbon atoms, or a therapeutically useful acid addition salt thereof.

Outstanding are the compounds of Formulae III and IV

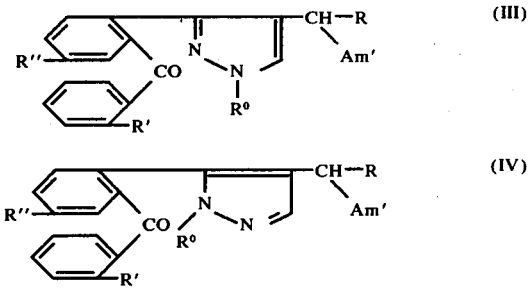

wherein R is hydrogen or methyl, $R^o$ is hydrogen, methyl, ethyl, n- or i-propyl,n-, i- or t-butyl, 2- or 3-(hydroxy, dimetylamino or diethylamino)-(ethyl or propyl) or benzyl, each of R' and R'' is hydrogen, methyl, fluoro or chloro and Am' is amino, dimethylamino or diethylamino, the methyl or ethylene ketal or thioketal, or a therapeutically useful acid addition salt thereof.

The compounds of this invention are prepared according to conventional methods, for example by converting in compounds of Formulae Va or b

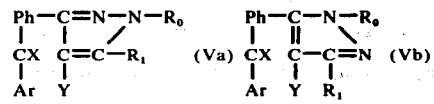

in which Y is a substituent capable of being converted into

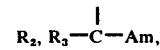

Y into said α-aminoalkyl group and, if desired, converting any resulting compound into another compound of the invention.

The substituent Y is, for example, a reactively esterified α-hydroxy-alkyl group, preferably such derived from a strong inorganic metalloidic acid, particularly a hydrohalic acid, e.g. hydrochloric or hydrobromic acid or sulfuric acid, or an organic sulfonic acid, such as a lower alkane or benzene sulfonic acid, e.g. methane, ethane, benzene or p-toluene sulfonic acid, or an α-phosphonium-alkyl group, e.g. an α-triphenyl-phosphonium halidealkyl group. Said groups Y are converted into α-Am-alkyl by condensation with H-Am or an alkali metal, e.g. sodium salt thereof.

Another substituent Y is, for example, an α-(nitro, oximino or imino)-alkyl group, or preferably a cyano or carbamoyl group, e.g. CO-Am, which groups can be converted into α-Am-alkyl by reduction. The above nitro compounds, nitriles or amides are advantageously reduced with the use of simple or complex light metal hydrides, such as boron hydride or alkali metal aluminum hydrides, e.g. lithium aluminum hydride. The above oximes or Schiff's bases, i.e. said α-oximino- or iminoalkyl compounds, as well as the α-nitroalkyl or cyano compounds, can also be reduced with catalytically activated or nascent hydrogen, such as hydrogen in the presence of nickel, platinum or preferably palladium catalysts, or generated electrolytically or by the action of metals on compounds with active hydrogen, such as acids or alcohols, e.g. zinc or iron and inorganic or organic acids, such as hydrohalic or lower alkanoic acids, or sodium or aluminum or their amalgams and lower alkanols.

Another process for the preparation of the compounds of Formulae I and II consists in hydrolyzing compounds of Formulae Vc or d

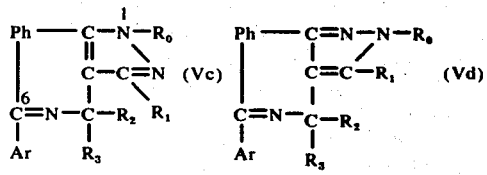

and, if desired, converting any resulting product into another compound of the invention.

Hydrolysis is advantageously performed under mildly acidic conditions, e.g. in the presence of aqueous and- /or alkanolic acids, e.g. said metalloidic acids, or the therapeutically useful acids listed below.

The carbinols of the invention (X=H+OH) are obtained from the ketones (X=O) by reduction as shown for the amides, advantageously with complex borohydrides, e.g. sodium boro- or lithium borohydride, or aluminum hydrides, e.g. lithium aluminum hydride in protic or non-protic solvents.

Another process for the preparation of the compounds of Formulae I and II consist in condensing a ketal or ether of Formula Ve

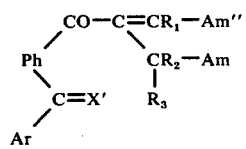

(Ve)

wherein $X'$ is said X different from O, S or H+OH and $Am''$ is said Am different from a primary or secondary amino group, with $R_1$-NH-NH$_2$ and if desired, converting any resulting compound into another compound of the invention.

The substitutent $X'$ is preferably lower alkoxy and alkylmercapto and $AM''$ preferably di-lower alkylamino. Said condensation is advantageously performed at elevated temperatures, for example between about 30° and 150° and in the presence or absence of a lower alkanol.

The compounds thus obtained can be converted into each other according to conventional methods. For example, resulting compounds containing at least one hydrogen atom attached to oxygen or nitrogen can be acylated, for example, with the use of reactive functional derivatives of the corresponding acids, such as halides or anhydrides thereof, e.g. acetyl or propionyl chloride, lower alkyl chloroformates, carbamoyl or thiocarbamoyl chlorides; acetic anhydride, ketene, isocyanates or isothiocyanates. Said primary or secondary amines can also be reacted with reactives esters of the respective alcohols, preferably derived from hydrohalic, aliphatic or aromatic sulfonic acids, e.g. lower alkyl or aralkyl chlorides, bromides, iodides; alkane- or benzenesulfonates, e.g. the mesylate or tosylate, or with corresponding aldehydes or ketones and reducing agents, e.g. formic acid, in order to obtain sec. or tert. amines respectively. Resulting ketals can also be converted into the ketone or thioketones, for example, by treating them with acidic agents, such as the above inorganic or organic acids. Finally, a resulting base can be converted into a corresponding acid addition salt, preferably with the use of a therapeutically useful acid or anion exchange preparation, or resulting salts can be converted into the corresponding free bases, for example, with the use of a base, such as a metal hydroxide, basic salt, ammonia, amine or cation exchange preparation, e.g. an alkali metal hydroxide or carbonate. Said acid addition salts are preferably such of therapeutically useful inorganic acids, such as strong metalloidic acids, for example hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycollic, lactic, malic, tartaric, citric, ascorbic, maleic, hydroxymaleic, pyroracemic, phenylacetic, benzoic 4-aminobenzoic, anthranilic, 4-hyroxybenzoic, salicylic, 4-aminosalicylic, embonic, nicotinic; methanesulfonic, ethanesulfonic, hydroxyethanesulfonic, ethylenesulfonic, halogen-benzenesulfonic, toluenesulfonic, naphthalenesulfonic or sulfanilic acid.

These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances. Resulting mixtures of isomers can be separated into the single isomers by methods in themselves known, e.g. by fractional distillation, crystallization and/or chromatography.

The invention further includes any variant of the present process in which an intermediate product obtainable at any stage of the process is used as starting material and any remaining steps are carried out, or the process is discontinued at any stage thereof, or in which the starting materials are formed under the reaction conditions, or in which the reaction components are used in the form of their salts. Mainly those starting materials should be used in the reactions of the invention that lead to the formation of those compounds indicated above as being especially valuable.

The starting material Vc to d is new and is considered as additional subject matter of the present invention. It is prepared according to the following formula scheme, which is illustrated by the examples herein:

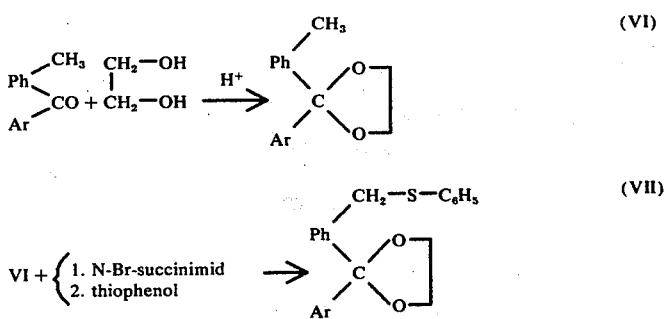

-continued
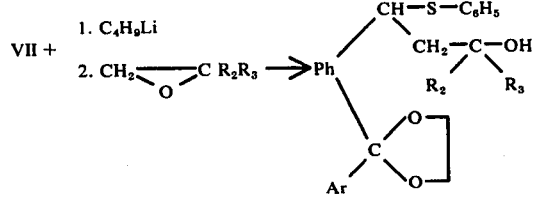
(VIII)
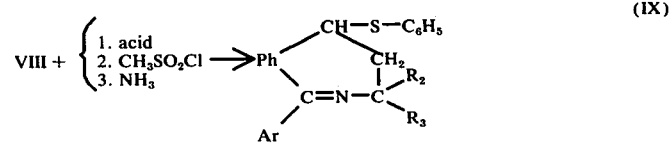
(IX)
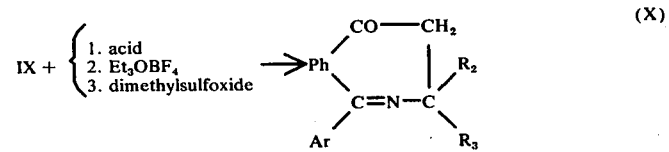
(X)
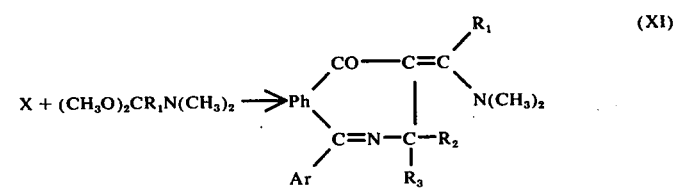
(XI)
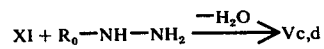
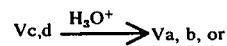
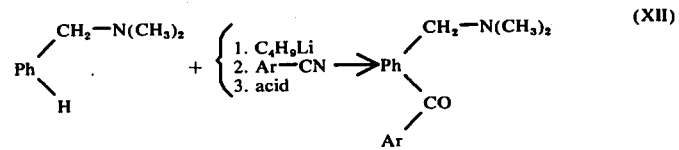
(XII)
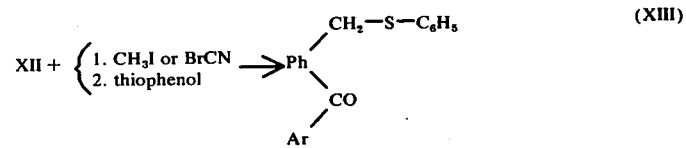
(XIII)
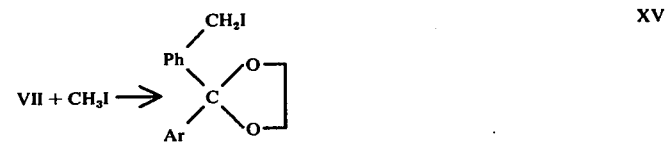
XV
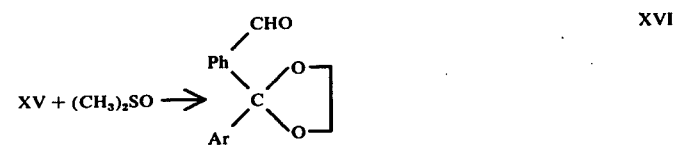
XVI
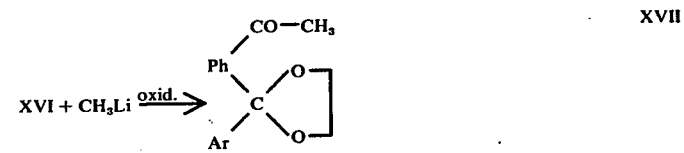
XVII

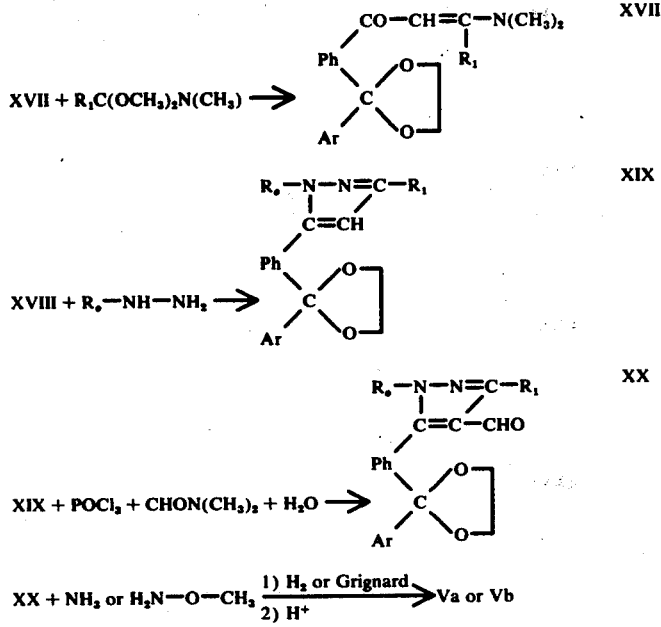
Another version for preparing the starting material of the formula Va or Vb is as follows:
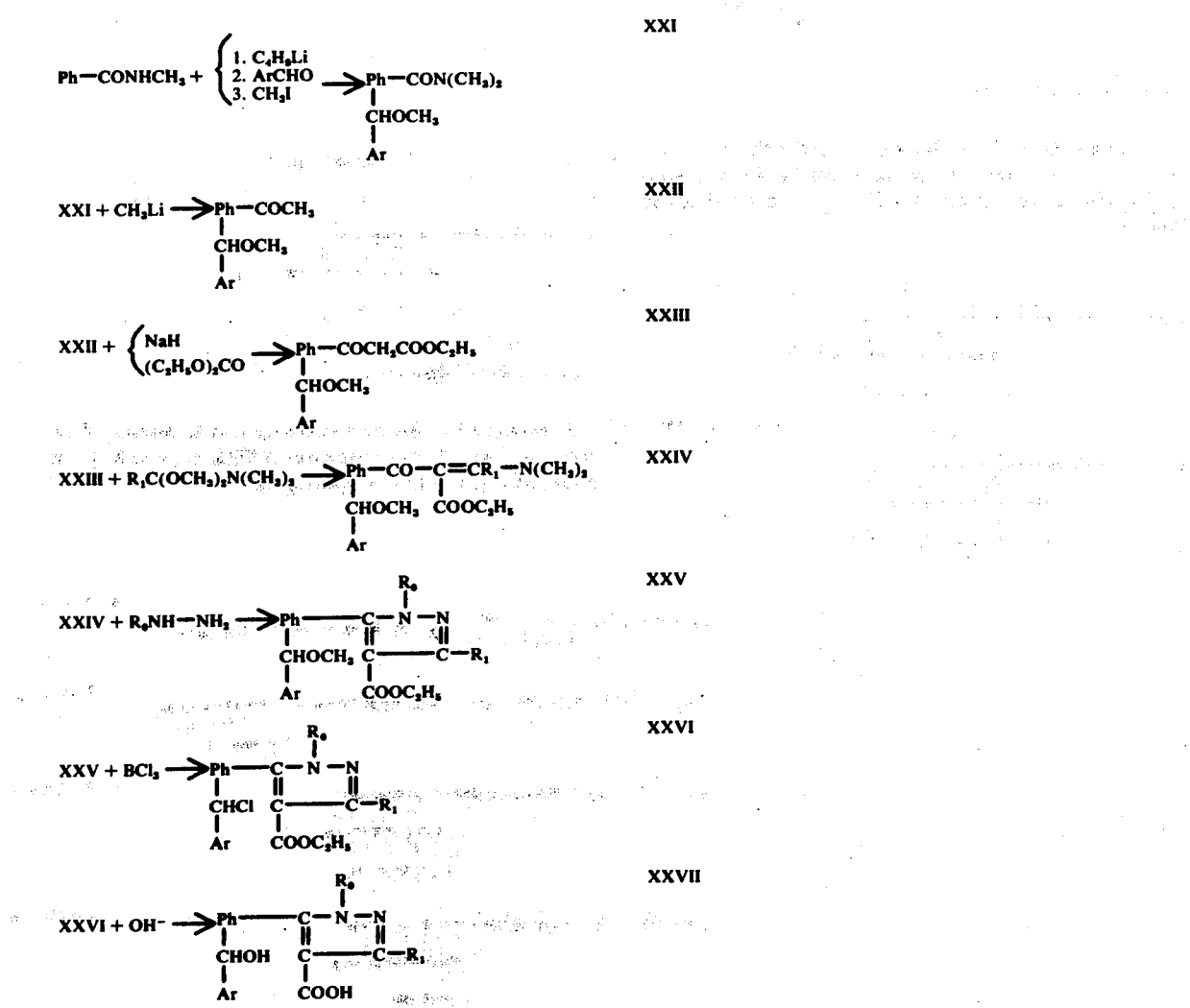

XXVII + H⁺ ⟶ 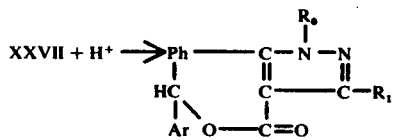

XXVIII + AlH₃ ⟶ 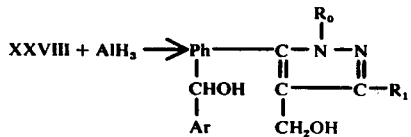

XXIX + {1. SOCl₂ / 2. [O]} ⟶ 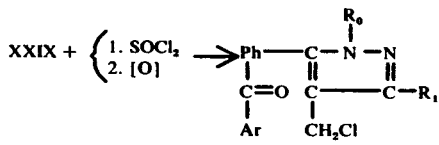

XXX + K-phthalimide ⟶ 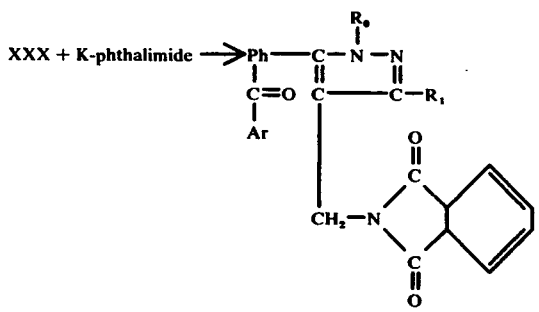

XXXI + H⁺ ⟶ Va or Vb

A modification of the above process for the manufacture of the intermediates of the formula XXX from a compound of the formula XXIX may be carried out as follows:

XXIX $\xrightarrow{\text{Tritylhalide}}$ 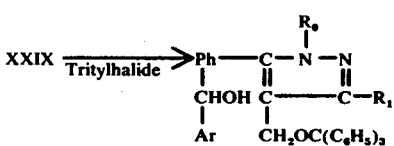   XXXII

XXXII $\xrightarrow{[O]}$ 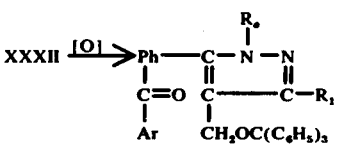   XXXIII

XXXIII $\xrightarrow{H^+}$ 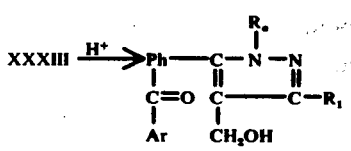   XXXIV

XXXIV $\xrightarrow[\text{pyridine}]{SOCl_2}$ XXX

A process for the manufacture of a tautomer of an intermediate of the formula XXXIV, in which R₀ is hydrogen, is the following one:

Ph—COCH₃ + {NaH / (C₂H₅O)₂CO} ⟶ Ph—CO—CH₂COOC₂H₅   XXXV

XXXV + R₁C(OCH₃)₂N(CH₃)₂ ⟶ 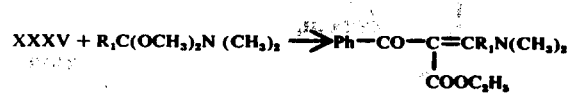   XXXVI

XXXVI + NH₂NH₂ ⟶ 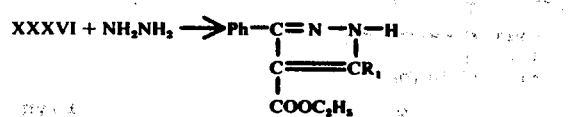   XXXVII

XXXVII + AlH₃ ⟶ 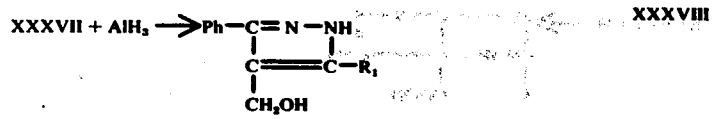   XXXVIII

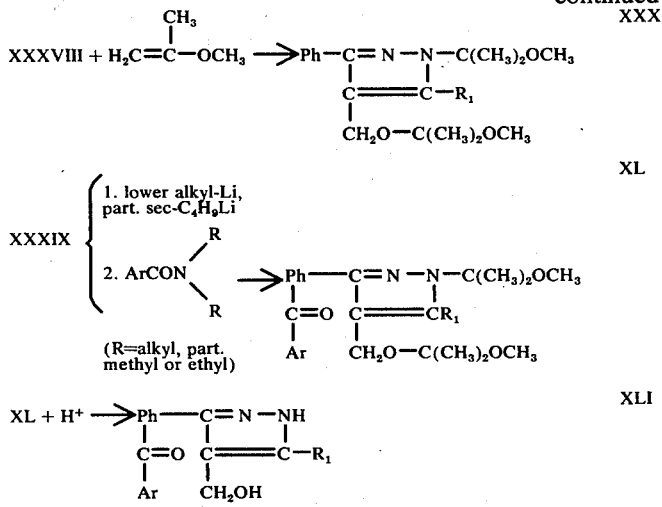

In a compound of the formula XLI, the hydrogen attached to the ring-nitrogen may be substituted by any of the organic residues specified for $R_o$; this substitution reaction is carried out as previously shown for compounds of the formulae I or II. In a compound of the formula XL, the imino nitrogen may be quaternized by treatment with a reactive ester of an alcohol, such as a lower alkyl fluorosulfonate, tri-lower alkyl-oxonium tetrafluoroborate and the like, followed by acid hydrolysis, whereby an intermediate of the formula XXXIV is obtained, in which $R_o$ is the residue of an alcohol. Alternatively, a compound of the formula XLI may be treated with a derivative of acrylic acid, such as acrylonitrile or a lower alkyl acrylate, in the N-Michael-addition product the imino nitrogen is then quaternized as previously shown or with another reactive ester of an alcohol, such as a lower alkyl halide, and the quaternary compound is then treated with a base, such as a tertiary amine or an alkali metal hydroxide or lower alkoxide in order to furnish a compound of the formula XXXIV, wherein $R_o$ is the residue of an alcohol.

The pharmacologically active compounds of the invention are useful in the manufacture of pharmaceutical compositions containing an effective amount thereof in conjunction or admixture with excipients suitable for either enteral or parenteral application. Preferred are tablets and gelatin capsules comprising the active ingredient together with a) diluents, e.g. lactose, dextrose, sucrose, mannitol, sorbitol, cellulose and/or glycine, b) lubricants, e.g. silica, talcum, stearic acid, its magnesium or calcium salt and/or polyethyleneglycol, for tablets also c) binders, e.g. magnesium aluminum silicate, starch paste, gelatin, tragacanth, methylcellulose sodium carboxymethylcellulose and/or polyvinylpyrrolidone, if desired, d) disintegrants, e.g. starches, agar, alginic acid or its sodium salt, enzymes of the binders or effervescent mixtures and/or e) absorbents, colorants, flavors and sweeteners. Injectable compositions are preferably aqueous isotonic solutions or suspensions, and suppositories are advantageously fatty emulsions or suspensions. They may be sterilized and/or contain adjuvants, such as preserving, stabilizing, wetting or emulsifying agents, solution promoters, salts for regulating the osmotic pressure and/or buffers. They may also contain other therapeutically valuable substances. Said pharmaceutical compositions are prepared according to conventional mixing, granulating or coating methods respectively and contain about 0.1 to 75%, preferably about 1 to 50% of the active ingredient.

The following examples, illustrating the invention, are not to be construed as being limitations thereon. Temperatures are given in degrees Centigrade and all parts wherever given are parts by weight.

EXAMPLE 1

The mixture of 130 mg of 5-chloro-2-(1-methyl-4-methoxyiminomethyl-5-pyrazolyl-2′-fluorobenzophenone ethylene ketal, 25 ml of diethyl ether and 100 mg of lithium alluminum hydride is stirred at room temperature for 16 hours. Thereupon 0.1 ml of water, 0.1 ml of 15% aqueous sodium hydroxide and 0.3 ml of water are added, the mixture filtered and the filtrate extracted with N hydrochloric acid. The acidic layer is separated, made basic with 2N aqueous sodium hydroxide, extracted with methylene chloride, the extract dried and evaporated, to yield the 5-chloro-2-(1-methyl-4-aminomethyl-5-pyrazolyl)-2′-fluorobenzophenone ethylene ketal of the Formula IV, wherein R=H, Am′=NH$_2$, R$^o$=CH$_3$, R′=F and R″=Cl, showing in the NMR-spectrum a singlet at $\delta$=3.03 and a triplet at $\delta$=8.0 ppm.

The mixture of 100 mg thereof, 10 ml of dioxane and 10 ml of 2N hydrochloric acid is refluxed for 1 hour under nitrogen and the dioxane evaporated. The aqueous solution is cooled, admixed to methylene chloride, made basic with 2N aqueous sodium hydroxide and extracted with diethyl ether. The extract is dried, filtered into the solution of 50 mg of phosphoric acid in 1 ml of ethanol and the precipitate filtered off, to yield the 5-chloro-2-(1-methyl-4-aminomethyl-5-pyrazolyl)-2′-fluorobenzophenone mono phosphate melting at 180°.

The starting material is obtained as follows: The solution of 10 g of 5-chloro-2′-fluoro-2-phenylmercaptomethyl-benzophenone ethylene ketal (Example 2) in 50 ml of methyl iodide is refluxed under nitrogen for 5 days. It is evaporated and the formed methyl phenyl thioether distilled off at 60°/0.1 mm Hg, to yield the 5-chloro-2′fluoro-2-iodomethyl-benzophenone ethylene ketal.

The mixture of 9.6 g thereof, 5 g sodium bicarbonate and 50 ml of dimethylsulfoxide is stirred for 20 minutes at 110°, cooled and poured onto ice. The mixture is extracted with diethyl ether, the extract washed with water and saturated aqueous sodium chloride, dried, evaporated and the residue recrystallized from diethyl ether-hexane, to yield the 5-chloro-2'-fluoro-2-formyl-benzophenone ethylene ketal melting at 103°–105°.

To the solution of 1.6 g thereof in 60 ml of diethyl ether, 3 ml of 2.3 molar methyl lithium in diethyl ether are added while stirring and cooling with ice. After 5 minutes 20 ml of water are added cautiously, the organic layer separated, washed with saturated aqueous sodium chloride, dried and evaporated, to yield the 5-chloro-2'-fluoro-2-(1-hydroxy-ethyl)-benzophenone ethylene ketal showing in the NMR-spectrum a doublet a $\delta=1.1$ ppm (in deuterochloroform).

To the solution of 1.8 g thereof in 100 ml or diethyl ether, 25 ml of the solution (obtained from 100 g of sodium dichromate dihydrate, 300 ml of water, 136 ml of concentrated sulfuric acid and diluting it with water to 500 ml) are added while stirring. After 40 minutes the mixture is poured on ice, the organic phase separated and washed with aqueous sodium bisulfite, water, aqueous sodium bicarbonate and saturated aqueous sodium chloride. It is dried and evaporated, to yield the 2-acetyl-5-chloro-2'-fluorobenzophenone ethylene ketal showing in the NMR spectrum a singlet at $\delta=2.4$ ppm.

The mixture of 1.1 g thereof and 7 ml of dimethyl formamide dimethylacetal is refluxed for 16 hours and evaporated under reduced pressure, to yield the 5-chloro-2-(3-dimethylaminoacryloyl)-2'-fluoro-benzophenone ethylene ketal showing in the NMR-spectrum a broad singlet at $\delta=2.7$ ppm.

The mixture of 1.3 g thereof, 0.3 g of methylhydrazine and 25 ml of ethanol is refluxed for 7 hours under nitrogen and evaporated. The residue is chromatographed on silica gel and the column eluted first with benzene, then diethyl ether and the ether eluate collected, to yield the 5-chloro-2'-fluoro-2-(1-methyl-5-pyrazolyl)-benzophenone ethylene ketal showing in the NMR-spectrum a singlet at $\delta=3.1$ and a doublet at $\delta=5.95$ ppm.

The solution of 650 mg thereof in 2.7 ml of ethylene dichloride is added dropwise to the complex, prepared from 265 mg of dimethylformamide and 555 mg of phosphorus oxychloride, while cooling with ice, and dissolved in 1.8 ml of ethylene dichloride, while stirring and the mixture is refluxed for 2 hours under nitrogen. After cooling the solution of 2.45 g of sodium acetate trihydrate in 3.6 ml of water is added and the mixture refluxed for 15 minutes. It is diluted with methylene chloride and water, the organic layer separated and dried, to yield the 5-chloro-2'-fluoro2-(1-methyl-4-formyl-5-pyrazolyl)-benzophenone ethylene ketal, showing in the NMR-spectrum a band at $\delta=9.13$ ppm.

The mixture of 660 mg thereof, 3 ml of pyridine and 170 mg of O-methyl-hydroxylamine hydrochloride is stirred for 16 hours at room temperature and evaporated under reduced pressure. The residue is taken up in chloroform and the solution filtered through a short column of silica gel, to yield the desired methoxime.

EXAMPLE 2

The mixture of 3.25 g of 8-chloro-6-(2-fluorophenyl)-1-methyl-1H,4H-pyrazolo-[4,3-d](2)benzazepine, 100 ml of 0.5N sulfuric acid and 15 ml of ethanol is stirred under nitrogen at room temperature for 2 days. The resulting solution is cooled to 0°, transferred into a separatory funnel, made basic with ice-cold 30% aqueous sodium hydroxide and quickly extracted with diethyl ether. The extract is dried filtered into the mixture of 1.2 g of 85% phosphoric acid and 50 ml ethanol and the precipitate collected, to yield the mono phosphate identical with that of Example 1, m.p. 180°.

Analogously the 5-chloro-2-(1-methyl-4-aminomethyl-5-pyrazolyl)-benzophenone monooxalate is obtained, melting at 163°–165°.

The starting material is prepared as follows: The solution of 141 g of $\alpha$,p-dichlorotoluene in 200 ml tetrahydrofuran is added dropwise to an ice-cold saturated solution of dimethylamine in 1 liter of tetrahydrofuran and the mixture stirred for 2 days at 25°. It is diluted with diethyl ether, washed with 2N aqueous sodium hydroxide, the organic layer dried, evaporated, the residue distilled and the fraction boiling at 106°/12 mm Hg collected, to yield the N,N-dimethyl-4-chlorobenzylamine.

To the solution of 81.6 g thereof in 1.5 lt of diethyl ether 360 ml of 1.6 molar n-butyl lithium in hexane are added dropwise while stirring at 0°–5° under nitrogen. After 3 hours the solution of 58 g of 2-fluorobenzonitrile in 1.5 lt of diethyl ether is added dropwise while stirring, the mixture refluxed for 3 hours and stirred at room temperature for 16 hours. Thereupon crushed ice and 265 ml of 5N hydrochloric acid are added, the mixture refluxed for ½ hour, cooled and the aqueous layer separated. It is made basic with 30% aqueous sodium hydroxide, extracted with methylene chloride, the extract dried, evaporated and the residue dried in a high vacuum at 100°, to yield the 5-chloro-2'fluoro-2-dimethylaminomethyl-benzophenone melting at 91°–92°.

To the solution of 138 g thereof in 3.2 lt of methylene chloride, that of 55 g of cyanogen bromide in 300 ml of methylene chloride is added dropwise while stirring and cooling with ice. After stirring overnight, the mixture is evaporated under reduced pressure at 40°. The residue is taken up in 2.4 lt of methanol, 56.8 ml of thiophenol are added, followed by 596 ml of N methanolic sodium hydroxide, the mixture stirred for 2 hours at 0° and overnight at room temperature. It is cooled again, filtered and the residue washed with methanol, to yield the 5-chloro-2'-fluoro-2-phenylmercaptomethyl-benzophenone melting at 81°–82°.

The mixture of 144.6 g thereof, 386 g of p-toluenesulfonic acid, 800 ml of ethylene glycol and 3 lt of benzene is refluxed at the water separator for 19 days and evaporated under reduced pressure, to yield the corresponding ethylene ketal melting at 69°.

To the solution of 24.2 g thereof in 285 ml of dry tetrahydrofuran, 46.2 ml of 1.6 molar n-butyl lithium in hexane are added while stirring under nitrogen at −67° to −70°. After one hour 100 ml of 6 molar ethyleneoxide in tetrahydrofuran are added during 5 minutes, the temperature allowed to rise to −35° and the mixture stirred for 2 hours at room temperature. It is evaporated under reduced pressure, the residue taken up in 165 ml of dioxane, 165 ml of 2N hydrochloric acid are added and the mixture refluxed for one hour. It is concentrated under reduced pressure to about half its volume, the concentrate extracted with methylene chloride, the extract dried and evaporated, to yield the 5-chloro-2-(3-hydroxy-1-phenylmercaptopropyl)-2'-fluorobenzophenone.

To the mixture of 26 g thereof, 16 ml of N,N-diisopropylethylamine and 360 ml of diethyl ether, 9.2 ml of methane-sulfonyl chloride are added dropwise while stirring at 0°. After 16 hours the mixture is washed with ice cold 5% hydrochloric acid, ice water and ice cold aqueous sodium carbonate, dried and evaporated under reduced pressure and below 30°. The residual methane-sulfonate is taken up in 220 ml of methanol, saturated with ammonia, while stirring and after 2 hours the solution is again saturated with ammonia. It is allowed to stand at room temperature for 27 days, the precipitate (B) formed filtered off and the filtrate evaporated. The residue is taken up in diethyl ether, the solution extracted with 2N sulfuric acid, the aqueous solution made basic with 30% aqueous sodium hydroxide and extracted with methylene chloride. The extract is dried, evaporated, the residue combined with (B) and recrystallized from acetone, acidified with ethereal hydrogen chloride to yield the 8-chloro-1-(2-fluorophenyl)-5-phenylmercapto-3,4-dihydro-2-benzazepine hydrochloride melting at 184°–185°.

The solution of 34.8 g thereof in 340 ml of methylene chloride is combined with 300 ml of 1.25 molar triethyloxonium tetrafluoroborate in methylene chloride while stirring under nitrogen. After 68 hours the mixture is evaporated under reduced pressure, the residue dissolved in 500 ml or dimethylsulfoxide and the solution stirred under nitrogen at 55° for 6 hours. It is evaporated under reduced pressure, the residue taken up in diethyl ether, the solution washed with water and extracted with 5% hydrochloric acid. The pH of the acidic solution is adjusted to 8 with sodium carbonate and the mixture extracted with diethyl ether. The extract is washed with water and saturated aqueous sodium chloride, the washings re-extracted with diethyl ether, the combined extracts dried, evaporated and the residue recrystallized from diethyl ether with the aid of charcoal, to yield the 8-chloro-1-(2-fluorophenyl)-3,4-dihydro-2-benzazepin-5-one melting at 107°–109°.

The mixture of 3.4 g thereof and 275 ml of dimethylformamide-dimethylacetal is refluxed for 75 minutes and the excessive reagent removed under reduced pressure at a temperature not exceeding 135°. The residue is crystallized from diethyl ether, to yield the 8-chloro-4-dimethylamino-methylidene-1-(2-fluorophenyl)-3,4-dihydro-2-benzazepin-5-one melting at 224°–226°.

2g thereof are added to the solution of 0.7 g of methylhydrazine in 100 ml of ethanol, the mixture refluxed for 45 minutes and evaporated under reduced pressure. The residue is recrystallized from ethyl acetate-hexane, to yield the 8-chloro-6-(2-fluorophenyl)-10a-hydroxy-1-methyl-3a,10a-dihydro-1H,4H-pyrazolo-[4,3-d](2)benzazepine melting at 114°–115°.

The solution of 1.74 g thereof in 60 ml of chloroform is stirred with 100 ml of 0.1 N hydrochloric acid for 15 minutes, the pH of the aqueous phase adjusted to 8 with aqueous sodium carbonate and the mixture again stirred for 5 minutes. The organic layer is separated, dried, evaporated and the residue recrystallized from diethyl ether-hexane, to yield the 8-chloro-6-(2-fluorophenyl)-1-methyl-1H,4H-pyrazolo [4,3-d](2)benzazepine melting at 128°–130°. The corresponding dihydrochloride melts at 190° with decomposition.

EXAMPLE 3

The solution of 13 g of 8-chloro-6-(2-fluorophenyl)-1-methyl-1H,4H-pyrazolo [4,3-d](2) benzazepine in 50.7 g of formic acid and 31.2 ml of 37% aqueous formaldehyde is refluxed for 10 hours. It is evaporated under reduced pressure, the residue taken up in methylene chloride and poured on ice and excess 30% aqueous sodium hydroxide. Separation of the organic layer, drying and removal of the solvent results in a solid product which, on neutralization of an acetone solution with ethereal hydrogen chloride, yields the 5-chloro-2-(1-methyl-4-dimethylaminomethyl-5-pyrazolyl)-2'-fluorobenzophenone hydrochloride melting at 225°–227°.

EXAMPLE 4

The solution of 1.86 g of 5-chloro-2-(1-methyl-4-dimethylaminomethyl-5-pyrazolyl)-2'-fluorobenzophenone in 100 ml of ethanol is stirred for 2½hours at room temperature with 500 mg sodium borohydride. It is evaporated under reduced pressure and the residue shaken with methylene chloride and 5% aqueous sodium hydroxide. After drying the organic layer and removal of the solvent, the residue is crystallized from diethyl ether-hexane, to yield the α-[5-chloro-2-(1-methyl-4-dimethylaminomethyl-5-pyrazolyl)-phenyl]-2-fluorobenzyl alcohol melting at 125° to 127°; the hydrochloride thereof melts at 225°–230°.

EXAMPLE 5

Preparation of 10,000 tablets each containing 25 mg of the active ingredient:

| Formula: | |
|---|---|
| 5-chloro-2-(1-methyl-4-aminomethyl-5-pyrazolyl)-2'-fluorobenzophenone mono-phosphate | 250.00 g |
| Lactose | 1,956.00 g |
| Corn starch | 90.00 g |
| Polyethylene glycol 6,000 | 90.00 g |
| Talcum powder | 90.00 g |
| Magnesium stearate | 24.00 g |
| Purified water | q.s. |

PROCEDURE:

All the powders are passed through a screen with openings of 0.6 mm. Then the drug substance, lactose, talcum, magnesium stearate and half of the starch are mixed in a suitable mixer. The other half of the starch is suspended in 45 ml of water and the suspension added to the boiling solution of the polyethylene in 180 ml of water. The paste formed is added to the powders which are granulated, if necessary, with an additional amount of water. The granulate is dried overnight at 35°, broken on a screen with 1.2 mm openings and compressed into tablets using concave punches with 7.1 mm diameter, uppers bisected.

Preparation of 10,000 capsules each containing 10 mg of the active ingredient:

| Formula: | |
|---|---|
| 5-chloro-2-(1-methyl-4-aminomethyl-5-pyrazolyl)-2'-fluorobenzophenone mono-phosphate | 500.0 g |
| Lactose | 2,350.0 g |
| Talcum powder | 15.0 g |

PROCEDURE:

All the powders are passed through a screen with openings of 0.6 mm. Then the drug substance is placed in a suitable mixer and mixed first with the talcum, then with the lactose until homogenous. No. 2 capsules are filled with 300 mg of the mixture, using a capsule filling machine.

EXAMPLE 6

A solution of 0.208 g of 3-[4-chloro-2-(2-fluoro-benzoyl)-phenyl]-2-methyl-4-phthalimidomethyl-pyrazole in 2 ml of concentrated hydrochloric acid and 2 ml of water is refluxed for 16 hours under an atmosphere of nitrogen. The solution is cooled with ice, made alkaline by adding a 15% aqueous sodium hydroxide solution and the product is extracted with methylene chloride. The organic layer is dried over anhydrous sodium sulfate and the solvent is evaporated to give a residue consisting of a mixture of 8-chloro-6-(2-fluorophenyl)-1-methyl-1H,4H-pyrazolo[4,3-d](2)benzazepine and mainly of the 5-chloro-2-(1-methyl-4-aminomethyl-5-pyrazolyl)-2'-fluorobenzophenone. Conversion of said residue into its phosphate as shown in Example 1 yields the identical compound melting at 180°.

The starting material is prepared as follows: To a mixture of 1250 ml of a 40% aqueous solution of methylamine and 1250 ml of methylene chloride, cooled in an ice bath, is added with stirring a solution of 500 g of 4-chlorobenzoyl chloride in 625 ml of methylene chloride. After the addition (50 minutes), the mixture is stirred for an additional 2 hours. The white precipitate is filtered off and air dried and the methylene chloride layer of the filtrate is dried and evaporated to give the crude 4-chloro-N-methyl-benzamide, which, after crystallization from 1200 ml of methanol, melts at 158°–161°; an additional amount of the product is recovered from the mother liquor, m.p. 158°–160°.

In a 3-necked flask equipped with thermometer, nitrogen inlet and dropping funnel, 84.75 g of 4-chloro-N-methylbenzamide is dissolved in 3000 ml of dry tetrahydrofuran and cooled to −45° while stirring under nitrogen atmosphere. When this temperature is reached, 660 ml of a 1.6 molar solution of n-butyl-lithium in hexane are added at such a rate, that the temperature does not exceed −40°. After the addition is complete, the cooling bath is removed and the temperature is allowed to raise to +10°. The mixture is then cooled in an ice bath and 65.6 g of 2-fluoro-benzaldehyde in 100 ml tetrahydrofuran is added in one batch. The bath is removed and the mixture is then stirred at room temperature for 2¼ hours; the pinkish color of the precipitate changes to a light grey. The flask is cooled again, 160 ml of methyl iodide is added and the reaction mixture is stirred at room temperature for 68 hours. The tetrahydrofuran is then removed under reduced pressure, the residue is taken up in about 1000 ml of diethyl ether and shaken with a mixture of ice water. After separation, the organic layer is washed with a saturated aqueous sodium chloride solution and dried over anhydrous sodium sulfate. The aqueous layers are reextracted with an additional portion of diethyl ether. Removal of the solvent leaves the 4-chloro-2-(2-fluoro-α-methoxybenzyl)-N,N-benzamide as an oily residue, which is directly used in the subsequent step.

A solution of 142 g of the dry 4-chloro-2-(2-fluoro-α-methoxy-benzyl)-N,N-dimethyl-benzamide in 1400 ml of toluene is cooled to −45° under an atmosphere of nitrogen. Then, a solution of 780 ml of a 1.7 molar solution of methyl lithium in diethyl ether is added at a rapid rate but without allowing the temperature to exceed −40°. The temperature is then allowed to slowly raise to room temperature. One hour after the addition of the methyl lithium, the reaction is quenched with ice/water, the organic layer is separated, washed with a saturated aqueous solution of sodium chloride and dried over anhydrous sodium sulfate. The aqueous layers are reextracted with diethyl ether. After evaporation of all solvents, the residue is crystallized from hexane to give the 4-chloro-2-(2-fluoro-α-methoxy-benzyl)-acetophenone, m.p. 59°–61°.

A solution of 85.3 g of the 4-chloro-2-(2-fluoro-α-methoxy-benzyl)-acetophenone in 370 ml of diethyl carbonate is added to a cooled (ice bath) suspension of 17.2 g of sodium hydride (55% in mineral oil, washed with diethyl ether to free it from the mineral oil) in 180 ml of diethyl carbonate. After the addition, the reaction mixture is stirred at room temperature for 2½ days, then diluted with diethyl ether. Ice is added and the pH is adjusted to 6 by adding hydrochloric acid and an aqueous sodium dihydrogenphosphate solution. After separation, the organic layer is washed with a saturated aqueous solution of sodium chloride, dried over sodium sulfate and evaporated to dryness. All aqueous layers are reextracted with diethyl ether. The ethyl 3-[4-chloro-2-(2-fluoro-α-methoxy-benzyl)-phenyl]-3-oxo-propionate is obtained as a liquid residue, which is used in the next step without further purification.

A solution of 107 g of the crude ethyl 3-[4-chloro-2-(2-fluoro-α-methoxy-benzyl)-phenyl]-3-oxo-propionate in 200 ml of dry dimethylformamide is refluxed for 1 hour with 84 ml of dimethylformamide-dimethylacetal under an atmosphere of nitrogen. Then, all solvent and excess reagent are removed at a pressure of 12 mm Hg. The residue, consisting of ethyl 3-[4-chloro-2-(2-fluoro-α-methoxy-benzyl)-2-dimethylaminomethylene]-3-oxo-propionate and containing some dimethylformamide, is directly used in the next step.

A solution of 127 g of the crude ethyl 3-[4-chloro-2-(2-fluoro-α-methoxy-benzyl)-2-dimethylaminomethylene]-3-oxo-propionate in 1500 ml of ethanol is refluxed for 1 hour with 25 g of methyl hydrazine under an atmosphere of nitrogen. Then, all solvent and volatile reagent are removed at a pressure of 12 mm Hg, and the residue is crystallized from 400 ml of diethyl ether to give product A, m.p. 128°–130°. Charcoal treatment of the mother liquor and evaporation to 150 ml, provides a product B, m.p. 114°–116°. Product A represents one isomeric (rotameric) form of the 3-[4-chloro-2-(2-fluoro-α-methoxy-benzyl)-phenyl]-4-ethoxycarbonyl-2-methyl-pyrazole, whereas product B is primarily the other isomeric (rotameric) form of the product, contaminated with a small amount of the first isomer.

To a solution of 20.1 g of 3-[4-chloro-2-(2-fluoro-α-methoxy-benzyl)-phenyl]-4-ethoxycarbonyl-2-methyl-pyrazole in 250 ml methylene chloride is added 54 ml of a 1.4 molar boron trichloride solution in methylene chloride, and the mixture is stirred during 16 hours. Ice/water is then added; the organic layer separated, washed with a saturated solution of sodium chloride and dried over anhydrous sodium sulfate. The aqueous layers are reextracted with methylene chloride. After removal of the solvent, the 3-[4-chloro-2-fluoro-benzyl)-phenyl]-4-ethoxycarbonyl-2-methyl-pyrazole is obtained as the solid residue, which is directly used in the next step.

A solution of the 3-(4-chloro-2-(α-chloro-2-fluoro-benzyl)-phenyl]-4-ethoxycarbonyl-2-methyl-pyrazole in 200 ml of dioxane is refluxed for 4 hours with 75 ml of a 2N aqueous solution of sodium hydroxide. The mixture is evaporated, the residue is shaken between diethyl ether and water, the basic aqueous layer is separated and acidified with 35 ml of 5N hydrochloric acid and extracted twice with methylene chloride. Drying of the organic layer over anhydrous sodium sulfate and evaporation of the solvent produces a foamy residue, comprising the 4-carboxy-3-[4-chloro-2-(2-fluoro-α-hydroxy-benzyl)-phenyl]-2-methyl-pyrazole, which is directly used in the subsequent step.

A solution of 20.3 g of the crude 4-carboxy-3-[4-chloro-2-(2-fluoro-α-hydroxy-benzyl)-phenyl]-2-methyl-pyrazole in 500 ml of toluene is refluxed with 1 g of p-toluenesulfonic acid using a water separator for 16 hours while stirring; the starting material starts to precipitate at the beginning but redissolves on further refluxing. The mixture is cooled, the toluene is evaporated using a rotary distillation apparatus until a product starts to precipitate. The mixture is then cooled, and a first crop of 8-chloro-6-(2-fluoro-phenyl)-1-methyl-4-oxo-1H,6H-pyrazolo-[4,3-d](2)benzoxepine, m.p. 198°–200°, can be collected. The mother liquor is washed with a cold aqueous solution of sodium carbonate, dried and evaporated. Crystallization of the residue from a mixture of diethyl ether and toluene provides an additional crop of the product, m.p. 219°–220°.

The aluminum hydride used in the following step is prepared according to the procedure described by Brown et al, J. Am. Chem. Soc., Vol. 90 page 2934 (1968): a mixture of 3.05 g of lithium aluminum hydride in 52 ml of dry tetrahydrofuran is stirred for 2 hours at room temperature. An additional 68 ml of tetrahydrofuran are added. The mixture is cooled in an ice bath and then treated with 2.14 ml of concentrated sulfuric acid, which is added dropwise. Vigorous stirring is continued for 1 hour at room temperature. The supernatant solution of the aluminum hydride is directly used in the following reaction.

To an ice-cooled solution of approximately 33 m moles of aluminum hydride in 50 ml of tetrahydrofuran is added a solution of 6.86 g of 8-chloro-6-(2-fluoro-phenyl)-1-methyl-4-oxo-1H,6H-pyrazolo[4,3-d](2)benzoxepine in 150 ml of dry tetrahydrofuran under an atmosphere of nitrogen. After the addition, the mixture is stirred an additional 30 minutes in an ice bath. The excess of the reagent is then carefully destroyed by adding water; 50 ml of 2N hydrochloric acid is added to dissolve the voluminous precipitate. The two layers are separated, the organic layer is washed with a saturated aqueous sodium chloride solution and dried over anhydrous sodium sulfate. All aqueous layers are reextracted with diethyl ether. The residue (consisting of a mixture of thermally interconvertible isomers) is taken up in 100 ml of dioxane and refluxed for 2 hours. The dioxane is then removed under reduced pressure and the residue is crystallized from 30 ml of diethyl ether to give the thermodynamically more stable isomer of the 3-[4-chloro-2-(2-fluoro-α-hydroxy-benzyl)-phenyl]-4-hydroxymethyl-2-methyl-pyrazole, m.p. 152°–155°. The mother liquor is equilibrated again by refluxing in dioxane and an additional amount of the product, m.p. 153°–155°, can be collected.

A solution of 1.04 g of 3-[4-chloro-2-(2-fluoro-α-hydroxybenzyl)-phenyl]-4-hydroxymethyl-2-methyl-pyrazole in 25 ml of anhydrous tetrahydrofuran is cooled in a dry nitrogen atmosphere in an ice bath. Then, 7.15 ml of a 0.504 molar solution of thionyl chloride in benzene is added through a dropping funnel, followed by 7.25 ml of a 0.496 molar solution of pyridine in tetrahydrofuran. After the addition, a precipitate forms, the mixture is stirred for 30 minutes in the ice bath and is then treated with 20 ml of 4N aqueous sulfuric acid. The mixture is stirred for another 30 minutes in the ice bath. The two layers are then separated in a separatory funnel, washed with a concentrated solution of sodium chloride and the aqueous layers are reextracted with diethyl ether. After drying the organic layers, the solvent is removed at a temperature of below 35°.

The residue is then dissolved in 50 ml of diethyl ether, cooled in an ice bath and 5 ml of an aqueous chromic acid solution (which is prepared by dissolving 100 g of sodium dichromate dihydrate in 300 ml of water, adding 136 ml of concentrated sulfuric acid and diluting the mixture to a volume of 500 ml with water) are added while stirring. After stirring for 30 minutes at 0°, the excess of the chromic acid is destroyed with an aqueous sodium sulfite solution. The mixture is diluted wth diethyl ether, transferred to a separatory funnel and the two layers are separated. After washing with water, reextraction of the aqueous layers with diethyl ether and drying over anhydrous sodium sulfate, the solvent is removed on the rotary still below 35° to give the 4-chloromethyl-3-[4-chloro-2-(2-fluoro-benzoyl)-phenyl]-1-methyl-pyrazole, which is directly used in the next step.

A solution of 1.0 g of the crude 4-chloromethyl-3-[4-chloro-2-(2-fluoro-benzoyl)-phenyl]-2-methyl-pyrazole in 15 ml of dry dimethylformamide is stirred at room temperature with 0.55 g of potassium phthalimide for 16 hours. The mixture is diluted with diethyl ether, washed twice with water and then with a saturated aqueous sodium chloride solution. The aqueous layers are reextracted with diethyl ether; the organic phase is dried over anhydrous sodium sulfate. After evaporation of the solvent, the residue is dissolved in 15 ml of diethyl ether, whereupon the product crystallizes. A first crop of the 3-[4-chloro-2-(2-fluoro-benzoyl)-phenyl]-2-methyl-4-phthalimidomethyl-pyrazole, m.p. 153°–155°, can be collected.

Alternatively the starting material is prepared as follows: A solution of 0.347 g of 3-[4-chloro-2-(2-fluoro-α-hydroxy-benzyl)-phenyl]-4-hydroxymethyl-2-methyl-pyrazole, 0.278 g of trityl chloride and 0.101 g of triethylamine in 15 ml of methylene chloride is stirred for 16 hours at room temperature. The solution is then filtered through a small column of neutral aluminum oxide. The column is washed with methylene chloride and the filtrate, containing the 3-[4-chloro-2-(2-fluoro-α-hydroxybenzyl)-phenyl]-2-methyl-4-trityloxymethyl-pyrazole, is used in the next step.

The above solution is added to a solution of 0.6 g of chromium trioxide and 0.95 g of pyridine in 15 ml of methylene chloride. After 15 minutes the solution is filtered through a small column of neutral aluminum oxide; the column washed with methylene chloride and the filtrate is evaporated to dryness. Toluene is added to the residue which contains some pyridine. The toluene is removed by evaporation under reduced pressure and the residue, containing the 3-[4-chloro-2-(2-fluoro-benzoyl)-phenyl]2-methyl-4-trityloxymethyl-pyrazole, is used without any further purification in the next step.

The above residue is dissolved in 15 ml of tetrahydrofuran and 4 ml of concentrated hydrochloric acid is added to the solution, which is then stirred for 3 hours at room temperature. The solvent is removed by evaporation under reduced pressure and the residue is treated with diethyl ether and a saturated solution of sodium bicarbonate. The ether solution is washed with water, dried over sodium sulfate and passed through a column of silica gel; the triphenyl carbinol is not retained on the column. After washing with diethyl ether, the column is eluted with tetrahydrofuran. The solvent is removed by evaporation to give the 3-[4-chloro-2-(2-fluoro-benzoyl)-phenyl]-4-hydroxymethyl-2-methyl-pyrazole as a colorless oil.

Alternatively, the 3-[4-chloro-2-(2-fluoro-benzoyl)-phenyl]-2-methyl-4-trityloxymethyl-pyrazole may be dissolved in acetic acid and treated with hydrogen bromide whereupon the trityl bromide is precipitated (and can be reused for tritylation) and the 3-[4-chloro-2-(2-fluoro-benzoyl)-phenyl]-4-hydroxymethyl-2-methyl-pyrazole will remain in the acetic acid solution.

To a solution of 0.295 g of the above keto alcohol in 15 ml of tetrahydrofuran is added 0.230 g of thionyl chloride in 5 ml of tetrahydrofuran, followed by 0.160 g of pyridine in 5 ml of tetrahydrofuran. The mixture is stirred at room temperature for 30 minutes and then treated with 10 ml of 1N hydrochloric acid. The organic phase is isolated, dried and evaporated to dryness yielding the 4-chloromethyl-3-[4-chloro-2-(2-fluoro-benzoyl)-phenyl]-2-methyl-pyrazole as a colorless oil.

To a solution of the above chloroketone in 5 ml of dimethylformamide is added an equivalent amount of potassium phthalimide. The mixture is stirred for 16 hours at room temperature and then diluted with diethyl ether. The organic solution is then washed with water and saturated aqueous solution of sodium chloride. After drying over sodium sulfate, the ether solution is evaporated to dryness. The oily residue is crystallized from diethyl ether to yield the 3-[4-chloro-2-(2-fluoro-benzoyl)-phenyl]-4-phthalimidomethyl-2-methyl-pyrazole, m.p. 153°–155°.

EXAMPLE 7

The solution of 7.8 g of 3-[4-chloro-2-(2-chloro-αmethoxy-benzyl)-phenyl]-2-methylpyrazole-4-carboxylic acid in 75 ml of methylene chloride and 6.7 diisopropyl ethylamine is stirred in an ice bath and 4.7 ml of thionyl chloride are added. The mixture is refluxed for 40 minutes, cooled and washed with ice-water. The organic layer is dried, evaporated and the residue taken up in 65 ml of tetrahydrofuran and the solution saturated with ammonia. After stirring at 25° for 16 hours, the mixture is diluted in diethyl ether, washed with water and brine, dried and evaporated. The residue is dissolved in 300 ml of diethyl ether and the solution refluxed for 16 hours with 2 g of lithium aluminum hydride. After destroying the excess reagent and filtering off the precipitate, the filtrate is washed with diluted hydrochloric acid. The acidic layer is basified with aqueous sodium hydroxide and extracted with methylene chloride. The extract is dried, evaporated, the residue taken up in ethyl acetate and the solution acidified with hydrogen chloride, to yield the 3-[4-chloro-2-(2-chloro-α-methoxy-benzyl)-phenyl]-4-aminomethyl-2-methylpyrazole hydrochloride melting at 260°–262°.

The starting material is prepared analogously as the 2-fluoro analog of Example 6.77 g of 3-(4-chloro-2-(2-chloro-αmethoxy-benzyl)-phenyl]ethoxycarbonyl-2-methyl-pyrazole are dissolved in 900 ml of ethanol and 240 ml of N aqueous sodium hydroxide and the solution is refluxed for 2 hours. After cooling the aqueous phase is separated, washed with diethyl ether and acidified with hydrochloric acid. It is extracted with methylene chloride, the extract dried and evaporated. The residue is recrystallized from 200 ml of diethyl ether to yield the 3-[4-chloro-2-(2-chloro-α-methoxy-benzyl)-phenyl]-2-methylpyrazole-4-carboxylic acid melting at 210°–213°.

EXAMPLE 8

The solution of 5.8 g of 3-[4-chloro-2-(2-chloro-α-methoxy-benzyl)-phenyl]-2-methylpyrazole-4-carboxylic acid in 50 ml of methylene chloride and 5 ml of diisopropyl ethylamine is cooled in an ice bath, 3.5 ml of thionyl chloride are added and the mixture is refluxed for 40 minutes. It is diluted with methylene chloride, quickly washed with ice-water, dried and evaporated. The residue is taken up in 50 ml of tetrahydrofuran, the solution saturated with methylamine and stirred over-night. The mixture is evaporated, the residue taken up in methylene chloride and the solution washed with aqueous sodium carbonate. It is dried, evaporated and the residue taken up in 200 ml of diethyl ether and 1.2 g of lithium aluminum hydride are added. The mixture is refluxed for 16 hours, decomposed with 1.2 ml of water, 1.2 ml of 15% aqueous sodium hydroxide and 3.6 ml of water, the precipitate filtered off and the filtrate evaporated. The residue is taken up in ethanol, the solution neutralized with ethanolic oxalic acid and the precipitate collected, to yield the 3-[4-chloro-2-(2-chloro-α-methoxy-benzyl)-phenyl]-4-methylaminomethyl-2-methylpyrazole oxalate melting at 154° with decomposition.

I claim:
1. A compound of the formula

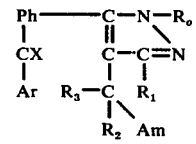

wherein Ph is 1,2-phenylene and Ar is phenyl, both of said radicals are unsubstituted or substituted by one or two, of the same or different substituents selected from the group consisting of lower alkyl, lower alkoxy, halo and trifluoromethyl, $R_o$ is hydrogen, lower alkyl, hydroxy-lower alkyl, lower alkoxy- lower alkyl, amino-lower alkyl, lower alkylamino-lower alkyl, di-lower alkylamino-lower alkyl, Ar or Ar-lower alkyl, Am is amino, mono- or di-lower alkylamino, wherein the additional chain-nitrogen, or oxygen atom is separated from the ring-nitrogen by at least 2 carbon atoms, each of $R_1$, $R_2$, and $R_3$ is hydrogen or lower alkyl, and X is oxo or thio; simple or mixed, open or cyclic lower alkyl or alkylene ketals thereof; or a pharmaceutically acceptable acid addition salt thereof.

2. A compound as claimed in claim 1, in which formula Ph is 1,2-phenylene, (lower alkyl)-1,2-phenylene, (lower alkoxy)-1,2-phenylene, (halo)-1,2-phenylene, or (trifluoromethyl)-1,2-phenylene, Ar is H—Ph, $R_o$ is hydrogen, lower alkyl, hydroxy—$C_mH_{2m}$, lower alkoxy-$C_mH_{2m}$, amino- $C_mH_{2m}$, lower alkylamino-$C_mH_{2m}$, di-lower alkylamino-$C_mH_{2m}$ or H-Ph-$C_nH_{2n}$, Am is amino, mono- or di-lower alkylamino, m is an integer from 2 to 4, and n such from 0 to 4, each of $R_1$, $R_2$ and $R_3$ is hydrogen or lower alkyl, and X is oxo or thio, or the simple or mixed, open or cyclic lower alkyl or alkylene ketals thereof or a pharmaceutically acceptable acid addition salt thereof.

3. A compound as claimed in claim 1, in which formula Ph is 1,2-phenylene, (alkyl)-1,2-phenylene or (halo)-1,2-phenylene, Ar is H-Ph, $R_o$ hydrogen, alkyl, 2-hydroxyethyl, 2- or 3-hydroxypropyl, 2-dialkylaminoethyl, 2- or 3-dialkylaminopropyl or H-Ph-methyl, each of $R_1$, $R_2$, and $R_3$ is hydrogen or methyl, the group Am is amino or dialkylamino, X is oxo or thia or the ethylenedioxy derivative thereof, in which compounds alkyl has 1 to 4 carbon atoms, or a pharmaceutically acceptable acid addition salt thereof.

4. A compound as claimed in claim 3, and having the formula

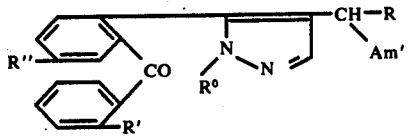

wherein R is hydrogen or methyl, $R^o$ is hydrogen, methyl, ethyl, n- or i-propyl, ni-,i- or t-butyl, 2-hydroxyethyl, 2- or 3-hydroxypropyl, 2-dimethylaminoethyl, 2- or 3-dimethylaminopropyl, 2-diethyl-aminoethyl, 2- or 3-diethylaminopropyl or benzyl, each of R' and R'' is hydrogen, methyl, fluoro or chloro and Am' is amino, dimethylamino or diethylamino, the methyl or ethylene ketal or thioketal, or a pharmaceutically acceptable acid addition salt thereof.

5. A compound as claimed in claim 4 and being the 5-chloro-2-(1-methyl-4-aminomethyl-5-pyrazolyl)-2'-fluorobenzophenone or a pharmaceutically acceptable acid addition salt thereof.

* * * * *